(12) United States Patent
Cooks

(10) Patent No.: US 11,389,321 B2
(45) Date of Patent: Jul. 19, 2022

(54) FEMALE CATHETER ASSEMBLY

(71) Applicant: Michael Cooks, Miami, FL (US)

(72) Inventor: Michael Cooks, Miami, FL (US)

( * ) Notice: Subject to any disclaimer, the term of this patent is extended or adjusted under 35 U.S.C. 154(b) by 166 days.

(21) Appl. No.: 16/687,832

(22) Filed: Nov. 19, 2019

(65) Prior Publication Data

US 2021/0145625 A1 May 20, 2021

(51) Int. Cl.
*A61F 5/455* (2006.01)
*A61J 1/10* (2006.01)
*A61F 5/443* (2006.01)

(52) U.S. Cl.
CPC ............ *A61F 5/4556* (2013.01); *A61F 5/455* (2013.01); *A61F 5/443* (2013.01); *A61J 1/10* (2013.01)

(58) Field of Classification Search
CPC ........ A61F 5/4556; A61F 5/455; A61F 5/443; A61J 1/10; A61G 9/006
See application file for complete search history.

(56) References Cited

U.S. PATENT DOCUMENTS

| | | | |
|---|---|---|---|
| 4,233,978 A | 11/1980 | Hickey | |
| 4,563,183 A | 1/1986 | Barrodale | |
| 4,886,508 A | 12/1989 | Washington | |
| 4,889,532 A * | 12/1989 | Metz | A61F 5/455 604/330 |
| 4,889,533 A * | 12/1989 | Beecher | A61F 5/4405 604/330 |
| D378,129 S | 2/1997 | Wexler | |
| 6,132,407 A * | 10/2000 | Genese | A61F 5/4405 222/559 |
| 6,151,721 A | 11/2000 | Whitefield | |
| 6,183,454 B1 | 2/2001 | Levine | |
| 2003/0163120 A1 * | 8/2003 | Harvie | A61F 5/455 604/544 |
| 2010/0094233 A1 * | 4/2010 | Ashworth | A61F 5/4556 604/317 |
| 2010/0185168 A1 * | 7/2010 | Graauw | A61F 5/4556 604/347 |
| 2011/0238023 A1 * | 9/2011 | Slayton | A61F 13/472 604/329 |
| 2012/0041400 A1 * | 2/2012 | Christensen | A61M 1/69 604/318 |

(Continued)

FOREIGN PATENT DOCUMENTS

WO  WO958169  11/1999

*Primary Examiner* — Benjamin J Klein
*Assistant Examiner* — Hans Kaliher

(57) ABSTRACT

A female catheter assembly for a discrete and comfortable solution to female urinary incontinence includes a collection unit having a partially cylindrical collection area and an inner band coupled around a perimeter of the collection area. The collection area is configured to cover from above a user's vagina to a user's perineum. A cover extends from a right side, a top side, and a left side of the inner band and an outer band is coupled to a perimeter of the cover. An inner surface of the collection unit has an adhesive coupled from the inner band to the outer band. The collection area has a drain aperture adjacent a bottom side. A hose extends from a drain port coupled to the drain aperture to a collection bag. A release tube is coupled to a lower aperture of the collection bag and a clamp is selectively engageable with the release tube.

12 Claims, 5 Drawing Sheets

(56) References Cited

U.S. PATENT DOCUMENTS

| | | | |
|---|---|---|---|
| 2012/0103347 A1* | 5/2012 | Wheaton | A61F 5/443 |
| | | | 128/885 |
| 2015/0112228 A1 | 4/2015 | Ekema | |
| 2017/0128255 A1* | 5/2017 | DeShazer | A61F 5/4405 |
| 2020/0046544 A1* | 2/2020 | Godinez | A61F 5/4408 |
| 2020/0206468 A1* | 7/2020 | Olson | A61M 25/02 |
| 2020/0375781 A1* | 12/2020 | Staali | A61F 5/441 |

* cited by examiner

FEMALE CATHETER ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to catheters and more particularly pertains to a new catheter for a discrete and comfortable solution to female urinary incontinence.

BRIEF SUMMARY OF THE INVENTION

An embodiment of the disclosure meets the needs presented above by generally comprising a collection unit having a partially cylindrical collection area and an inner band coupled around a perimeter of the collection area, the collection area being configured to cover from above a user's vagina to a user's perineum. A cover extends from a right side, a top side, and a left side of the inner band and an outer band is coupled to a perimeter of the cover. An inner surface of the collection unit has an adhesive coupled from the inner band to the outer band. The inner band is configured to adhere to a user's labial folds and the outer band is configured to adhere a user's outer vaginal area and the perineum. The collection area has a drain aperture extending therethrough adjacent a bottom side. The collection unit is flexible and is configured to form to the shape of the user's vaginal area. A drain port is coupled to the drain aperture and a hose is coupled to, and in fluid communication with, the drain port. A collection bag has an upper aperture extending through a top edge selectively engaged with a distal end of the hose and a lower aperture adjacent a bottom edge. A release tube is coupled to the lower aperture. A clamp is selectively engageable with the release tube to seal and alternatively unseal the release tube.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
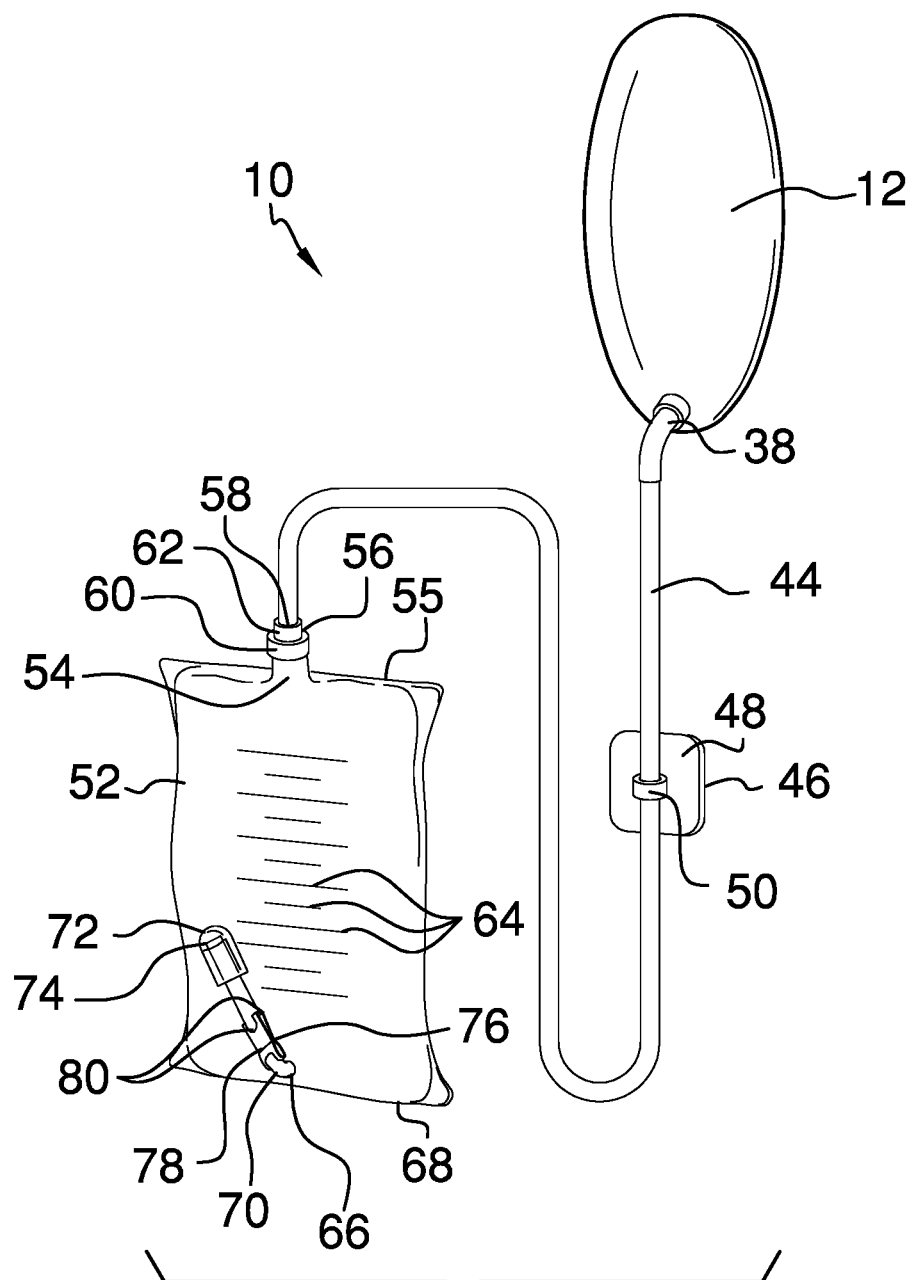
FIG. 1 is an isometric view of a female catheter assembly according to an embodiment of the disclosure.
Figure 2:
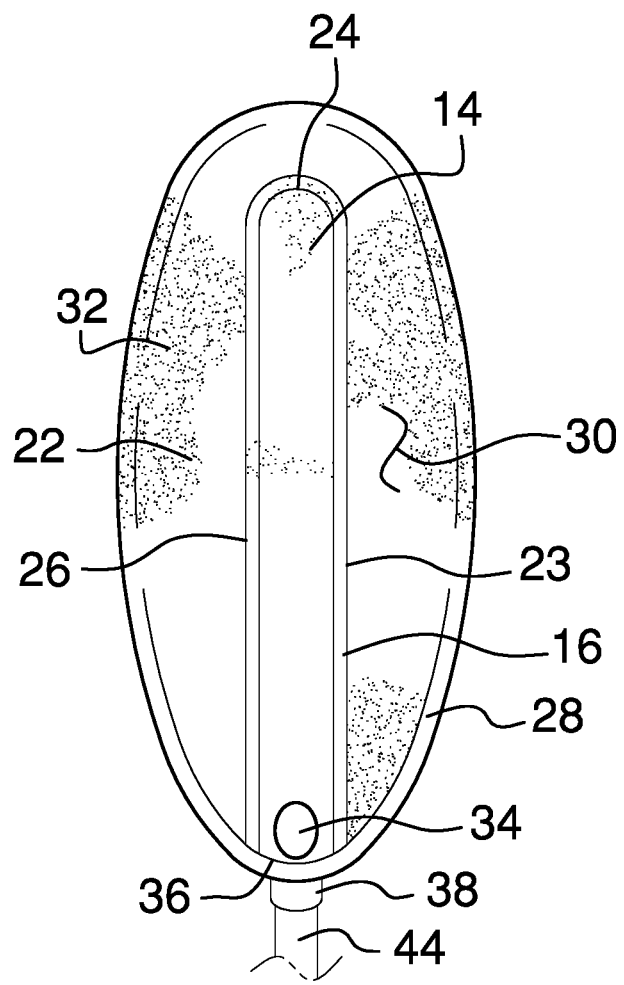
FIG. 2 is a rear elevation view of an embodiment of the disclosure.
Figure 3:
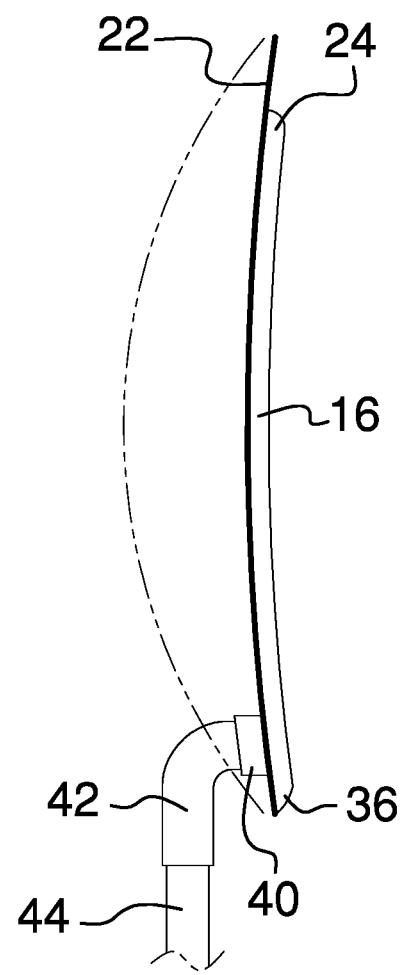
FIG. 3 is a side elevation view of an embodiment of the disclosure.
Figure 4:
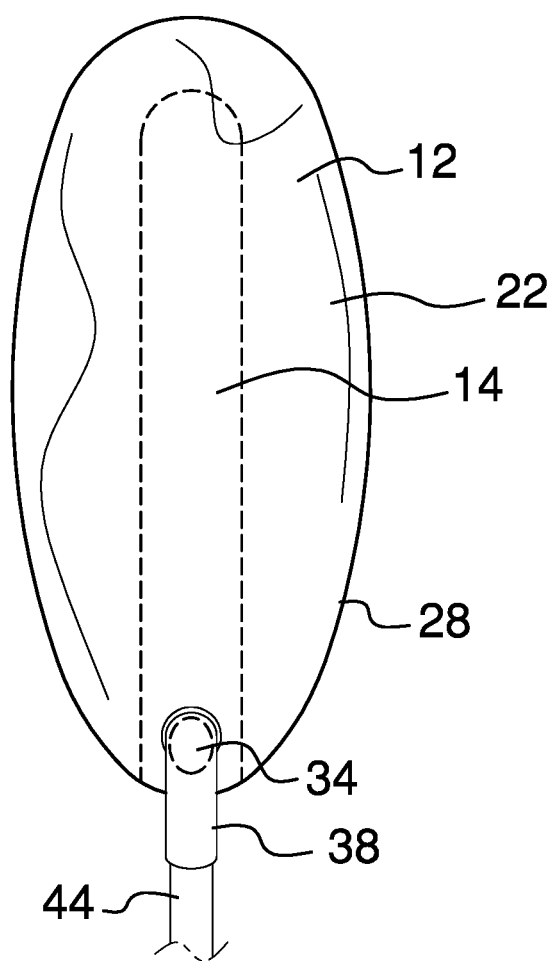
FIG. 4 is a front elevation view of an embodiment of the disclosure.
Figure 5:
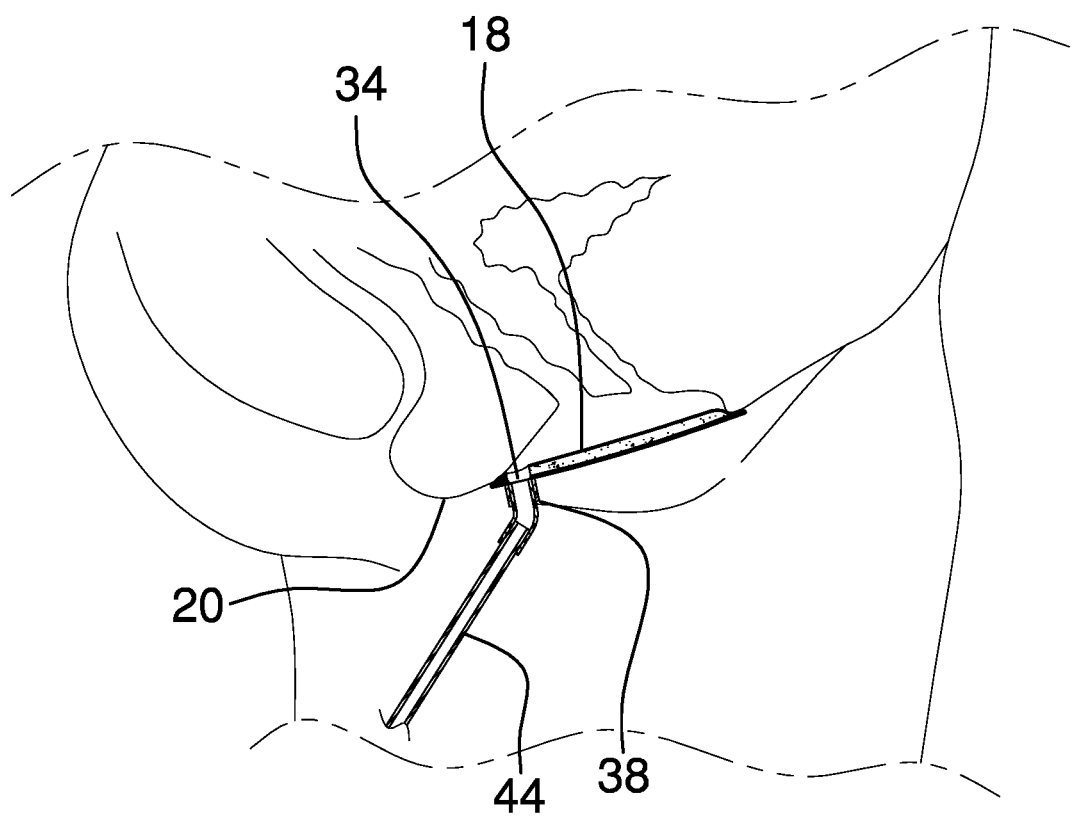
FIG. 5 is a cross-sectional in-use view of an embodiment of the disclosure.

With reference now to the drawings, and in particular to FIGS. 1 through 5 thereof, a new catheter embodying the principles and concepts of an embodiment of the disclosure and generally designated by the reference numeral 10 will be described.

As best illustrated in FIGS. 1 through 5, the female catheter assembly 10 generally comprises a collection unit 12 having a partially cylindrical collection area 14 and an inner band 16 coupled around a perimeter of the collection area 14. The collection area 14 is configured to cover from above a user's vagina 18 to a user's perineum 20. A cover 22 extends from a right side 23, a top side 24, and a left side 26 of the inner band 16. The top side 24 may be semicircular. An elliptical outer band 28 is coupled to a perimeter of the cover 22. An inner surface 30 of the collection unit has an adhesive 32 coupled from the inner band 16 to the outer band 28. The inner band 16 is configured to adhere to a user's labial folds and the outer band 28 is configured to adhere a user's outer vaginal area and the perineum 20. The collection area 14 has a drain aperture 34 extending therethrough adjacent a bottom side 36. The collection unit 12 is flexible and is configured to form to the shape of the user's vaginal area. When flattened, the inner band 16 protrudes past the inner surface 30. The collection unit 12 may be a soft silicone material and the adhesive 32 may be chlorhexidine gluconate for easy and irritation-free removal.

A drain port 38 is coupled to the collection unit 12. The drain port 38 comprises a collar 40 coupled to the drain aperture 34 and an elbow 42 coupled to the collar 40. The elbow 42 may be rigid to allow easy connection with the collar 40 which may be flexible and rubberized to create a liquid seal around the elbow 42. A hose 44 is coupled to, and in fluid communication with, the drain port 38. The hose 44 is selectively engageable within the elbow 42 and may be a soft silicone. A leg clip 46 has a base 48 and a sleeve 50 coupled to the base 48. The base 48 is adhesive and is configured to selectively adhere to a user's leg to guide the hose 44 and prevent accidental removal from the drain port 38. The sleeve 50 is coupled around the hose 44. The base 48 may be square and has rounded corners for user comfort.

A collection bag 52 is coupled to the hose 44. The collection bag 52 has a neck 54 extending from a top edge 55 and an upper aperture 58 extending through the neck 54. A rigid rim 56 is coupled to the neck 54 to selectively receive a distal end 58 of the hose. The rim 56 may have a wider grip portion 60 proximal the neck 54 and a thinner mouth portion 62 extending above the grip portion 60 to receive the hose 44. The grip portion 60 provides more surface area for the user to grip the rim 56 when inserting and removing the hose 44 from the collection bag 52. A front face 62 of the collection bag has a plurality of linear volume markings 64 to keep track of urination and a lower aperture 66 adjacent a bottom edge 68. A release tube 70 is coupled to, and in fluid communication with, the lower aperture 66 to empty the collection bag 52. A tip cap 72 selectively engages a tip end 74 of the release tube for sanitary purposes. A clamp 76 is selectively engageable with the release tube 70 to seal and alternatively unseal the release tube 70. The clamp 76 may have a hinge 78 and a pair of jaws 80 extending from the hinge on either side of the release tube 70. The pair of jaws 80 are selectively engageable to maintain a pinched position sealing the release tube 70 while the collection bag 52 is in use.

In use, the collection unit 12 is applied to sealingly enclose the vaginal area with the hose 44 coupled to the drain port 38. The base 48 of the leg clip is adhered to the user's leg and the clamp 76 is maintained with the jaws 80 in the pinched position. When desired, the clamp 76 is released and the collection bag 52 may be emptied through the release tube 70.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A female catheter assembly comprising:
    a collection unit, the collection unit having a partially cylindrical collection area, the collection area being configured to cover from above a user's vagina to a user's perineum, the collection unit having an inner band extending around the collection area, a cover extending from a right side, a top side, and a left side of the inner band, and an outer band coupled to a perimeter of the cover, the outer band extending fully around the perimeter of the cover, the inner band being U-shaped having opposing ends abutting the outer band, an inner surface of the collection unit having an adhesive coupled to and positioned continuously from the inner band to the outer band, the inner band being configured to adhere to a user's labial folds and the outer band being configured to adhere a user's outer vaginal area and the perineum, the collection area having a drain aperture extending therethrough adjacent a bottom side, the drain aperture being positioned adjacent to the outer band between the opposing ends of the inner band, the collection unit being flexible and configured to form to the shape of the user's vaginal area;
    a drain port coupled to the collection unit, the drain port being coupled to the drain aperture;
    a hose coupled to the drain port, the hose being in fluid communication with the drain port;
    a collection bag coupled to the hose, the collection bag having an upper aperture extending through a top edge selectively engaged with a distal end of the hose, the collection bag having a lower aperture adjacent a bottom edge;
    a release tube coupled to the collection bag, the release tube being coupled to the lower aperture; and
    a clamp coupled to the release tube; the clamp being selectively engageable with the release tube to seal and alternatively unseal the release tube.

2. The female catheter assembly of claim 1 further comprising the drain port comprising a collar coupled to the drain aperture and an elbow coupled to the collar, the elbow being rigid to allow easy connection with the collar and the hose.

3. The female catheter assembly of claim 2 further comprising the elbow being a 90° angle.

4. The female catheter assembly of claim 1 further comprising a leg clip, the leg clip having a base and a sleeve coupled to the base, the base being adhesive and configured to selectively adhere to a user's leg, the sleeve being coupled around the hose.

5. The female catheter assembly of claim 4 further comprising the base being square and having rounded corners.

6. The female catheter assembly of claim 1 further comprising the outer band being elliptical.

7. The female catheter assembly of claim 1 further comprising the collection bag having a neck extending from the top edge, the upper aperture extending through the neck, a rigid rim being coupled to the neck to selectively receive the distal end of the hose.

8. The female catheter assembly of claim 7 further comprising the rim having a wider grip portion proximal the neck and a thinner mouth portion extending above the grip portion, the mouth portion receiving the hose.

9. The female catheter assembly of claim 1 further comprising a front face of the collection bag having a plurality of linear volume markings.

10. The female catheter assembly of claim 1 further comprising a tip cap coupled to the release tube, the tip cap selectively engaging a tip end of the release tube.

11. The female catheter assembly of claim 1 further comprising the adhesive including chlorhexidine gluconate.

12. A female catheter assembly comprising:
    a collection unit, the collection unit having a partially cylindrical collection area, the collection area being configured to cover from above a user's vagina to a user's perineum, the collection unit having an inner band extending around the collection area, a cover extending from a right side, a top side, and a left side of the inner band, and an elliptical outer band coupled to a perimeter of the cover, the outer band extending fully around the perimeter of the cover, the inner band being U-shaped having opposing ends abutting the outer band, an inner surface of the collection unit having an adhesive coupled to and positioned continuously from the inner band to the outer band, the inner band being configured to adhere to a user's labial folds and the outer band being configured to adhere a user's outer vaginal area and the perineum, the collection area having a drain aperture extending therethrough adjacent a bottom side, the drain aperture being positioned adjacent to the outer band between the opposing ends of the inner band, the collection unit being flexible and configured to form to the shape of the user's vaginal area;

a drain port coupled to the collection unit the drain port comprising a collar coupled to the drain aperture and an elbow coupled to the collar, the elbow being rigid to allow easy connection with the collar;

a hose coupled to the drain port, the hose being in fluid communication with the drain port and selectively engageable within the elbow;

a leg clip, the leg clip having a base and a sleeve coupled to the base, the base being adhesive and configured to selectively adhere to a user's leg, the sleeve being coupled around the hose, the base being square and having rounded corners;

a collection bag coupled to the hose, the collection bag having a neck extending from a top edge and an upper aperture extending through the neck, a rigid rim being coupled to the neck to selectively receive a distal end of the hose, the rim having a wider grip portion proximal the neck and a thinner mouth portion extending above the grip portion, the mouth portion receiving the hose, a front face of the collection bag having a plurality of linear volume markings and a lower aperture adjacent a bottom edge;

a release tube coupled to the collection bag, the release tube being coupled to the lower aperture;

a tip cap coupled to the release tube, the tip cap selectively engaging a tip end of the release tube; and a clamp coupled to the release tube; the clamp being selectively engageable with the release tube to seal and alternatively unseal the release tube.

* * * * *